United States Patent [19]

Bucalo

[11] 3,932,223

[45] Jan. 13, 1976

[54] CULTURING MEDIUM

[76] Inventor: Louis Bucalo, 155 Roberts St., Holbrook, N.Y. 11741

[22] Filed: Jan. 7, 1975

[21] Appl. No.: 539,254

Related U.S. Application Data

[62] Division of Ser. No. 405,939, Oct. 12, 1973, Pat. No. 3,864,213.

[52] U.S. Cl. ............................................. 195/139
[51] Int. Cl.² ........................................... C12K 1/10
[58] Field of Search ........................ 195/103.5, 139

[56] References Cited
UNITED STATES PATENTS

| | | | |
|---|---|---|---|
| 3,341,427 | 9/1967 | Evans et al.................. | 195/103.5 R |
| 3,367,841 | 2/1968 | Buissiere et al............. | 195/103.5 R |

*Primary Examiner*—Lionel M. Shapiro
*Assistant Examiner*—Robert J. Warden
*Attorney, Agent, or Firm*—Steinberg & Blake

[57] ABSTRACT

A culturing article according to which one part of a wick is placed in engagement with a body fluid in order to check for the presence of suspected microorganisms. An opposed part of the wick is maintained out of engagement with the body fluid, so that by capillary action the body fluid will progress along the wick from the one part toward the opposed part thereof. The progress of the body fluid from the one part toward the opposed part of the wick is limited to achieve a density gradient according to which the body fluid is most dense at the one part of the wick which engages the body fluid while the body fluid becomes gradually less dense from the one part toward the opposed part of the wick, to provide a density gradient. A culture medium engages the wick to encourage predetermined microorganisms to grow, and at a certain portion of the density gradient the microorganisms will be very clearly evident. The wick as well as the culture medium may be in the form of a roll which is encapsulated to be enclosed at all except the part of the wick which engages the body fluid, or the wick and culture medium may take the form of separate layers. The culture medium may have portions of different properties for encouraging different microorganisms to grow, so that it becomes possible to check simultaneously for the presence of different microorganisms.

9 Claims, 7 Drawing Figures

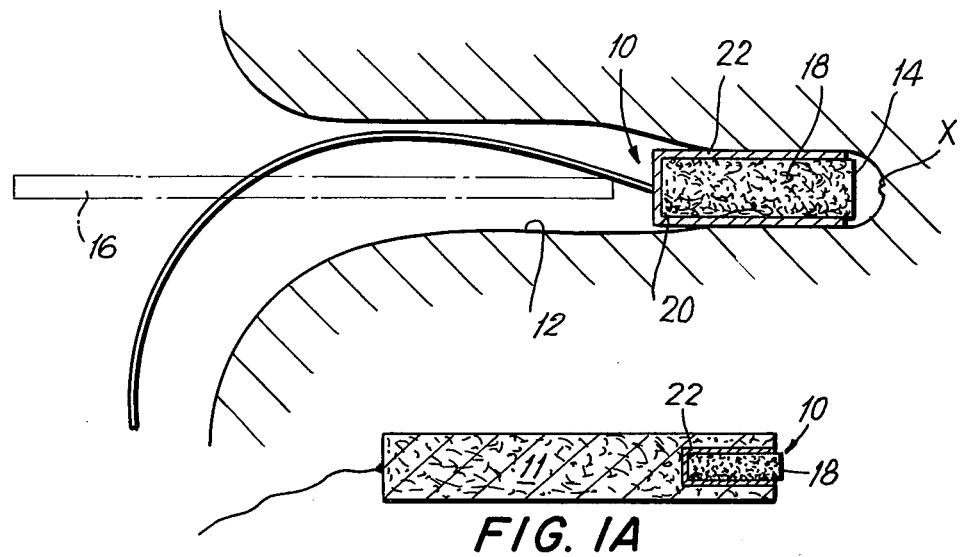
FIG. 1
FIG. 1A
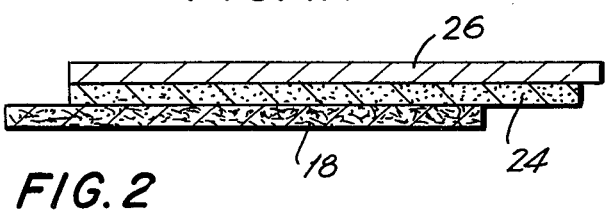
FIG. 2
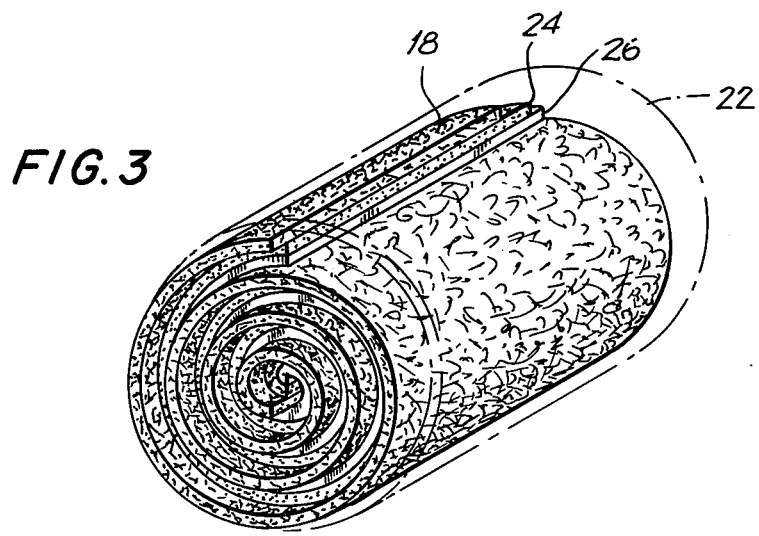
FIG. 3

OUTSIDE THE BODY | INSIDE THE BODY

CULTURING MEDIUM

CROSS REFERENCE TO RELATED APPLICATION

The present application is a division of copending application Ser. No. 405,939, filed Oct. 12, 1973 now U.S. Pat. No. 3,864,213, and entitled CULTURING METHOD.

BACKGROUND OF THE INVENTION

The present invention relates to culturing methods and articles.

Thus, the present invention more specifically relates to methods and articles to be used in order to determine the presence of microorganisms in body fluids.

At the present time in order to determine whether or not certain microorganisms are present in a body fluid, it is customary to take a swab of the area where the body fluid is located and transfer part of the body fluid by way of the swab to a culture medium which is placed in an incubator. After a certain time the culture medium is examined to determine whether or not the microorganisms are present.

A number of serious drawbacks reside in this conventional procedure for determining the presence of certain microorganisms. Thus, because the swab is stroked over only part of the area where the body fluid is located, it is easy to neglect to take a sample of that part of the body fluid where the microorganisms are located. For example in the case of a throat infection or in the case of a vaginal infection, it is possible for the swab to be moved over an area where there are no microorganisms even though microorganisms are present directly next to the area engaged by the swab. Under these conditions it is easy to neglect to determine the presence of microorganisms even though the microorganisms actually are in the body fluid.

Furthermore, when the body fluid is transferred by the swab to the culture medium and the culture medium is then placed in an incubator, the microorganisms are compelled to grow outside of the body under conditions quite different from those which prevail in the body. Thus while the microorganisms may grow readily under the conditions prevailing in the body cavity where the microorganisms are located, the conditions in the incubator may be unfavorable for growing the microorganisms, so that in this case also it is possible to fail to determine the presence of microorganisms.

In addition, even if the suspected microorganisms are transferred by the swab to the culture medium, the manner in which the microorganisms grow makes it extremely difficult to determine the presence thereof. Thus a number of different microorganisms are necessarily transferred by the swab to the culture medium. All of these microorganisms grow. The result is that when the culture medium is examined, an exceedingly confusing array of growths are visible. All of these growths are crowded together and spread out over the culture medium, with the result that it becomes extremely difficult to know for certain whether or not the particular microorganisms which are of interest are indeed present.

SUMMARY OF THE INVENTION

It is accordingly a primary object of the present invention to provide a culturing article which will avoid the above drawbacks.

In particular, it is an object of the present invention to provide a culturing article which will reliably indicate the presence of suspected microorganisms if indeed they are present in the body fluid which is checked.

Thus, it is an object of the present invention to provide a culturing article which will render suspected microorganisms visible with the greatest possible clarity if indeed they are present in the body fluid which is tested.

In addition it is an object of the present invention to provide a culturing article which will reliably check a body fluid for determining the presence of suspected microorganisms in such a way that if the microorganisms are indeed present they will not be missed by failure to check a certain part of the body fluid.

Furthermore, it is an object of the present invention to provide a culturing article which makes it possible for the microorganisms, if they are present, to grow under conditions identical with those which are present in the body, so that there will be no failure to recognize the presence of microorganisms resulting from the fact that an attempt is made to encourage them to grow under conditions different from that prevailing in the body where thier presence is suspected.

Also, it is an object of the invention to be capable of growing microorganisms in the body without the danger of intensifying infection in the body by encouraging the growth of microorganisms therein.

Furthermore, it is an object of the present invention to provide a culturing article which is exceedingly simple so that the article is inexpensive and convenient to manipulate.

Furthermore, it is well known that more than one microorganism may be present in a body fluid, so that different tests should be made to determine the presence of the different microorganisms. A further object of the present invention is to provide a culturing article which makes it possible for different tests of this type to be carried out simultaneously so that at one and the same time it is possible to check for the presence of a number of different microorganisms.

According to the present invention a wick is placed at only one part thereof in engagement with body fluid so that the body fluid is sucked into the wick. The body fluid will thus progress along the wick from the one part thereof which engages the body fluid toward an opposed part of the wick which is distant from the one part thereof. A culture medium is placed in engagement with the wick to encourage predetermined microorganisms to grow if they are present in the body fluid which progresses along the wick from the one part to the opposed part thereof due to capillary action. The extent to which the body fluid can progress along the wick from the one part to the opposed part thereof is limited for achieving in this way a density gradient where the body fluid is most dense at the one part which engages the body fluid and becomes of gradually lesser density toward the opposed part of the wick. Experience has shown that with such a density gradient the microorganisms if indeed they are present will become visible with the greatest possible clarity at a part of the density gradient.

BRIEF DESCRIPTION OF DRAWINGS

The invention is illustrated by way of example in the accompanying drawings which form part of this application and in which:

FIG. 1 is a schematic representation of a vagina with an article according to the present invention schematically shown in the vagina in engagement with the fluid at the cervix;

FIG. 1A shows, in section, the article of the invention incorporated into a tampon:

FIG. 2 is a sectional illustration of the wick, culture medium, and barrier which form a basic unit of the article of the invention;

FIG. 3 illustrates one embodiment of an article of the invention according to which the wick is encapsulated in a roll;

DESCRIPTION OF PREFERRED EMBODIMENTS

Figure 4:
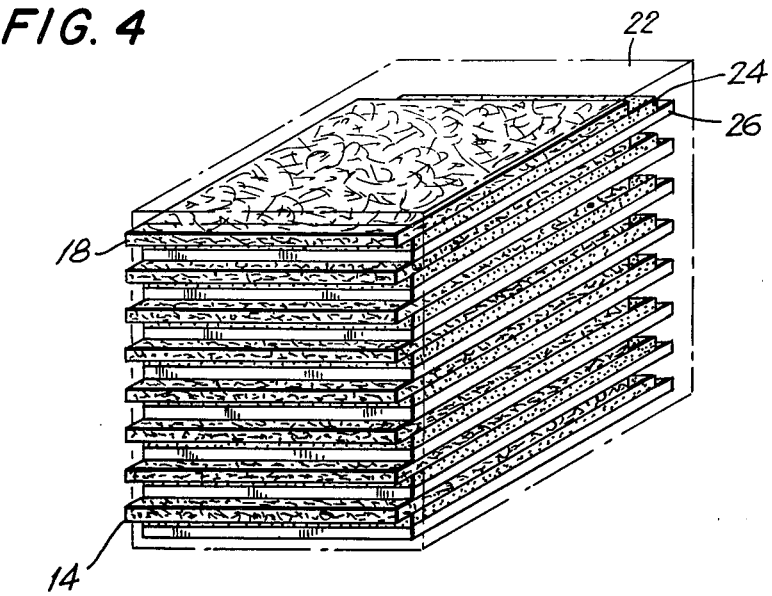
FIG. 4 shows an embodiment of the invention where the wick and other materials are in the form of substantially parallel layers.

Referring now to the drawings and to FIG. 1 in particular, there is schematically illustrated therein an article according to the present invention as used in connection with a sample of body fluid at the cervix. Thus, FIG. 1 illustrates an article 10 according to the present invention situated in a vagina 12. The right end 14, as viewed in FIG. 1, of the article 10 is introduced into the vagina 12 so that this right end 14 will engage body fluid at the region X, which represents the cervix. FIG. 1 schematically illustrates in dot-dash lines a rod 16 or the like which may be utilized to facilitate insertion of the article 10 of the invention.

As is illustrated in FIG. 1, this article 10 includes a wick 18 which when introduced in the above manner into the vagina 12 will have the end 14 in engagement with the body fluid at the cervix region X. Thus, the end region 14 of the wick 18 forms one part thereof which will engage the body fluid of which a sample is desired. Due to the capillary action of the wick, the body fluid will progress into the wick to progress therealong from the right toward the left, as viewed in FIG. 1, so that the body fluid will progress from the part 14 of the wick toward an opposed part 20 of the wick formed in the illustrated example by the end of the wick which is distant from the end 14.

According to a further feature of the invention the wick 18 is encapsulated within a casing 22 which is impervious to the body liquid, this casing 22 being made of a suitable plastic, for example. Thus, it will be seen that the casing 22 is cylindrical and completely surrounds the wick while also enclosing the end 20 of the wick. Thus it is only part of the wick which is formed by the end region 14 thereof which is exposed to the body fluid, so that in this way the body fluid will progress from the part 14 toward the part 20 of the wick.

The wick 18 is shown in FIG. 1 in a highly simplified manner. The actual construction is illustrated in section in FIG. 2 and in an elongated perspective view in FIG. 3. Thus, as is apparent from FIG. 2, the wick 18 is in the form of a suitable sheet material which may be made of any suitable cloth, foam or fibers. At one of its surfaces the wick 18 is engaged by the culture medium 24, such as agar, forming nourishment for microorganisms which are drawn into the wick by capillary action. The culture layer 24 is itself engaged by a barrier layer 26 which may be any suitable plastic or metal foil. If desired, the culture medium 24 may be sprayed directly onto the barrier layer 26 to harden thereon before being placed in engagement with the sheet material forming the wick 18. Also, the wick 18 can be impregnated with the culture medium 24 and then be applied against the barrier layer 26.

This multi-layer sheet structure which is shown in FIG. 2 is then rolled in the manner shown in FIG. 3 and inserted into means 22 which is shown in phantom lines in FIG. 3 so as to illustrate more clearly the details of the wick assembly. Because of the manner in which the sheet structure of FIG. 2 is rolled up, it is converted into a multiplicity of layers where the several layers are separated from each other by the barrier 26 with each layer having the culture medium 24 in engagement therewith. Of course, instead of being rolled it is possible to fold the sheet material back and forth upon itself to provide a differently shaped wick assembly, or several sheet structures as shown in FIG. 2 may be placed one on top of the other, as described below in connection with FIG. 4.

In order to facilitate withdrawal of the article 10, a suitable string 28 is fixed in any suitable way to the means 22 which encapsulates the wick structure 18. Before this device is withdrawn, however, it is permitted to remain in the position where the end 14 engages the body fluid for a given period of time. While in the above example the article 10 is shown in the vagina to have its end 14 engaging the cervix region, it is of course clear that the article of the invention may be used at a number of different locations in the body, such as the rectum, the ear, sinus or nasal passages, etc., for receiving body fluid in order to test the same for the presence of predetermined microorganisms. For this purpose the culture medium 24 will have a composition which will encourage the growth of the suspected microorganisms, and in fact the culture medium 24 may also include suitable compositions for preventing the growth of undesired microorganisms which may be present but in which there is no interest. In this way it is possible to prevent the disclosure of the suspected microorganisms from being confused by other microorganisms.

Moreover, as shown in FIG. 1A, the article 10 may be incorporated into a tampon 11 which is used during menses in a conventional manner. Upon removal of the tampon, article 10 can easily be removed and subsequently checked for the presence of a disease such as gonorrhea.

Depending upon where the article of the invention is used in the body, it may be left in the body for a period of time ranging from a minimum of approximately one-half hour to a maximum of approximately six hours.

Figure 5:
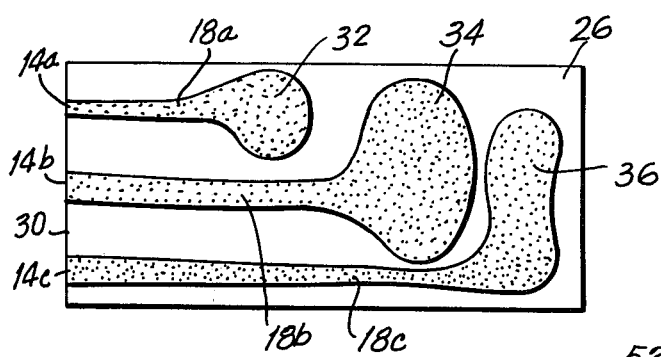
FIG. 5 schematically represents how the culture medium can be distributed in order to make simultaneously tests for the presence of a number of different microorganisms.

According to one of the features of the invention, it is possible, if desired, to select a time period long enough to permit the suspected microorganisms to grow so that they will be clearly visible when an inspection is made as pointed out below. Thus, by permitting the microorganisms to grow in the article of the invention while the latter remains in the body, the best possible conditions for growth of the suspected microorganisms are provided. In other words the microorganisms grow in the interior of the body under conditions prevailing in the interior of the body. It will be noted that means 22 forms a shield preventing growing microorganisms from intensifying a body infection, so that the article of the invention can be used with complete safety to grow microorganisms in the interior of the body under precisely the same conditions as those which are present in the body where the microorganisms are suspected. Thus any inhibiting of growth of the suspected microorganisms resulting from an attempt to carry out the growth in an artificially created atmosphere such as that which is present in an incubator is avoided according to this feature of the invention.

With the present invention a density gradient is formed. Thus, the body fluid will completely saturate the wick 18 at the exposed part 14 thereof, but the density of the body fluid while being a maximum at the part 14 will gradually reduce from the region 14 toward the region 20, so that as a result of this density gradient there will be one part of the density gradient where the microorganisms, if they are present, will be capable of growing into discrete colonies in sufficient numbers to be visible in the clearest possible manner. In other words at the region 14 of the greatest density there will be the confusion in identification as is normally encountered with present systems where a smear is transferred to a suitable culture medium and incubated. At the left end of the body fluid, as viewed in FIG. 1, where it has the least density and where in fact it practically disappears there will be an extremely small number of microorganisms so that there hardly will be any indication of the presence thereof if indeed they are present. However, between these two extremes there will be one region of the density gradient where the number of discrete colonies of suspected microorganisms is sufficiently great to render them apparent with the greatest possible clarity because the distribution therebetween is ideal and the possibility of confusion resulting from crowding together of a number of different microorganisms is completely avoided.

It will be noted particularly from FIG. 3 that the wick 18 is in fact in the form of an elongated relatively narrow strip of sheet material. Thus, the sheet material 18 may have a length on the order of 6 inches and a width of between 1 and 2 inches. Moreover, it is apparent that the end 14 of the wick is in the form of a relatively long edge of the sheet material, so that the body fluid progresses transversely across the narrow dimension of the wick toward the part 20 thereof, thus being distributed longitudinally of the sheet of wick material to provide in this way also an extremely clear indication of the presence of suspected micro-organisms. Furthermore, because of the wicking action, the body fluid progresses into the wick from all of the region where the part 14 is located, thus avoiding the possibility of missing a part of the area to be tested, as is commonly the case with conventional procedures according to which a suitable swab is simply stroked across the suspected area, with the result that very frequently that part of the area where the suspected microorganisms are located never forms part of the smear which is transferred to the culture medium which is then placed in an incubator.

As was pointed out above, it is not essential to roll the sheet structure shown in FIG. 2 in order to form a substantially cylindrically shaped wick assembly. As is illustrated in FIG. 4, it is possible to divide the sheet structure into a plurality of sections situated one upon the other as illustrated in FIG. 4. Thus, referring to FIG. 4 it will be seen that the uppermost layer is part of the sheet material 18 which forms the wick, while next to the latter is the layer of culture medium 24, and then this culture medium is engaged by the barrier layer 26. These layers form the unit of sheet structure shown in FIG. 2, and a plurality of these units are located one above the other as shown in FIG. 4 and encapsulated within a suitable means 22 which in the case of FIG. 4 has substantially the configuration of a cube which is open at one end so that the free edge regions of the wick portions 18 forming the ends 14 thereof will be exposed to the body fluid which is to be checked.

As was indicated above instead of having separate sheet sections as shown in FIG. 4, a continuous structure as shown rolled in FIG. 3 is instead folded back and forth upon itself. There are many different possibilities of the manner in which the sheet structure can be folded.

Furthermore, it is not absolutely essential that the part of the structure toward which the body fluid progresses be an edge region or end region distant from the part which engages the body fluid. It is perfectly possible to provide at an interior area of the wick a sufficient pressure to inhibit the progress of the body fluid all the way up to this interior area which then would form the part of the wick toward which the body fluid progresses. Thus, in this way it is possible to have more than one edge of the sheet material in engagement with the body fluid.

Furthermore, according to a further feature of the invention it is possible to check simultaneously for the presence of a number of different microorganisms. As is apparent from the above description the sheet material which forms the wick may have a fairly elongated configuration, so that in this way it becomes possible to situate at different parts of the wick different culture mediums having different properties for encouraging the growth of different microorganisms. When the wick is unrolled or when the sheets of FIG. 4 are examined, after application of a suitable staining medium, for example, the different culture mediums wil indicate at different parts of the wick whether or not different microorganisms have grown, and of course all of these microorganisms will be introduced simultaneously into the wick so that checking for the presence of different microorganisms is carried on at one and the same time. An arrangement of this type is particularly suitable for use in the rectum where a number of different disease microorganisms are likely to be present.

Furthermore, it is to be noted that because of the manner in which the wicking structure of the invention is constructed the level of oxygen will vary from the part 14 of the wick, which directly engages the body fluid, toward the part 20 which is most distant therefrom, and this factor also will contribute to the control which achieves the desired density gradient. Thus, in the case of FIG. 3, when the article is removed, the wick is displaced out of the means 22 and unrolled, whereas with the embodiment as shown in FIG. 4, the separate units each composed of the wick 18, the culture medium 24, and the barrier 26 are separated from each other. Of course in this case also the separate layers of culture medium 24 may have different properties to enable an assembly as shown in FIG. 4 to check simultaneously for the presence of different microorganisms.

It is also possible to provide an arrangement as shown in FIG. 5 according to which either the wick or the culture medium, with a barrier layer therebetween, are prepared in suitable patterns. FIG. 5 schematically illustrates a barrier layer 26 having thereon sheet material portions forming the illustrated wicks 18a, 18b, and 18c. These layers are separately impregnated with different culture mediums. However, it is also possible to provide an arrangement where the entire barrier 26 is covered by the sheet material which forms the wick and the culture medium is provided according to the patterns illustrated in FIG. 5. Also it is possible to place between the wick and culture medium an additional barrier layer having cutouts conforming to the patterns of FIG. 5. In all cases the different culture mediums at the different patterns will have different properties to encourage the growth of different microorganisms. The left edge 30 of the barrier layer 26 is the location of the feeding end of the wicking portions 18a–18c. Thus, all these portions have relatively narrow elongated sections extending up to the edge 30, and these sections terminate in the areas 14a, 14b, and 14c which form the parts which will directly engage the body fluid which is to be checked. This structure may be rolled around a horizontal axis as viewed in FIG. 5, for example, or several of the structures as shown in FIG. 5 may be situated one above the other. In any case the assembly will be encapsulated by a means 22 as described above, and the body fluid will enter along the narrow sections to reach the larger area sections as shown at the right of the narrow sections in FIG. 5. Thus, the wick portion 18a has a larger area section 32 where the body fluid can spread out so as to provide a clear indication of the presence of suspected microorganisms, the distribution being such that the density gradient will be most dense at the end 14a and least dense ata the region 32. In the same way, different microorganisms may show up at the area 34 where the body fluid enters through the portion 18b because the different culture medium, and in the same way at the area 36 a third type of suspected microorganism may appear. The advantage of the arrangement of FIG. 5 is that even with a relatively small sized construction it is possible to distribute the areas to be inspected over a relatively large portion of the structure. The arrangement as shown in FIG. 5 is designed from experience so that microorganisms of the type which will grow at the wicking portion 18a are known to appear at the part of the density gradient which is located at the area 32, while other microorganisms of the type which will respond to the culture medium at the wick portion 18b are known to grow at the distance of the area 34 from the feeding edge 30.

As a further feature of the invention it is possible to provide the sheet structure of the type shown in FIG. 2 in such a way that any desired edges are sealed while other edges are left open, so as to control the flow of body fluid and achieve a desired density gradient in this way also.

With a particular structure according to the present invention, the spiral type of device as shown in FIGS. 1 and 3 has a diameter of ¼ inch and has a length between the ends 14 and 20 of ¾ of an inch. However, considerable variation is possible in the size of the structure.

Although it has been pointed out above that one of the advantages which can be achieved with the invention is that the microorganisms are grown directly in the body cavity where their presence is suspected, it is of course also possible to remove the article of the invention prior to the time when the microorganisms have grown fully in the culture medium. Thus it is perfectly possible if desired to remove the article and place it in an incubator or the like. There will still be a considerable advantage achieved with the invention because the density gradient will provide an extremely clear showing of the suspected microorganisms and because the manner in which the sample is taken is far superior to the usual taking of smears.

Figure 6:
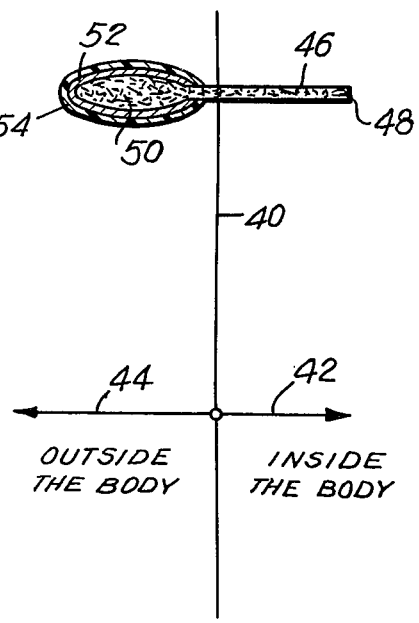
FIG. 6 schematically illustrates an embodiment of the invention according to which it is possible to check for the presence of microorganisms outside of the body while the wick extends into the interior of the body.

However, it is also possible to provide an arrangement as schematically illustrated in FIG. 6. Thus, referring to FIG. 6, the vertical line 40 schematically represents the outer surface of the body. To the right of the vertical line 40 is the interior of the body as indicated by the arrow 42, while to the left of the line 40 is the outside of the body where the surrounding atmosphere is located, as indicated by the arrow 44. As is schematically indicated in FIG. 6, it is possible to extend an elongated wick structure 46 into the interior of the body so as to have an end region 48 in engagement with the body fluid which is to be checked. This elongated portion 46 may have any suitable structure such as a tubular wicking structure, or a multi-fiber structure providing a fiber-feed system for the body fluid.

In any event, the elongated portion 46 forms an extension of the wick structure 50 which is situated at the exterior of the body as indicated in FIG. 6. This wick medium 50 is shown in FIG. 6 surrounded by the culture medium layer 52 which in turn is surrounded by the casing 54 which forms the means for enclosing the assembly of the wick and culture medium. Thus, the body fluid will travel freely along the portion 46 of the wick to reach the portion 50 thereof, but at the portion 50 a density gradient will be provided for the reasons set forth above and as a result the required density gradient will be achieved with the density of the body fluid gradually diminishing from the right toward the left of the casing 54 as viewed in FIG. 6. Thus, after a desired time the structure of FIG. 6, can be removed and if desired, the material 50 and the culture medium 52 can be placed in a suitable incubator if the microorganisms have not yet grown. However, it is perfectly possible for the microorganisms to grow within the casing 54 where the assembly at the exterior of the body is held next to the body so as to have a suitable growth atmosphere resulting from body heat. Therefore with an arrangement as shown in FIG. 6 it is possible for a patient to "wear" the device with only the elongated wick portion 46 extending into the body while the exterior structure is maintained next to the body in any suitable way at the exterior thereof. It is clear from the arrangement of FIG. 6 that configurations different from those of FIGS. 3 and 4 are possible since the same density gradient will be present in the wick portion 50, and after the casing 54 is removed the structure in the interior thereof can be checked for the presence of suspected microorganisms.

It is thus clear that with the above method and article of the invention it becomes possible to avoid many of the drawbacks resulting from conventional procedures and articles. An extremely effective check for the presence of suspected microorganisms can be provided with the method and article of the invention.

What is claimed is:

1. In an article for testing the presence of predetermined microorganisms, a wick having one part adapted to be placed in engagement with a body fluid and an opposed part distant from said one part, a culture medium for encouraging the growth of predetermined microorganisms, said culture medium engaging the wick and extending from the region of said one part thereof toward said opposed part thereof, and means enclosing at least part of the wick and culture medium for exposing said one part of said wick so that said one part can be placed in engagement with a body fluid and for limiting the distribution of the body fluid along said wick from said one part toward said opposed part thereof in a manner providing a degree of saturation of the body fluid in the wick which is gradually reduced from said one part toward said opposed part of the wick to provide a density gradient of the body fluid extending from said one part toward said opposed part of the wick.

2. The combination of claim 1 and wherein the wick is in the form of a sheet material having an edge region which forms said one part of the wick.

3. The combination of claim 2 and wherein the sheet material is arranged in a plurality of layers each of which is engaged by the culture medium, and a barrier situated between the culture medium engaging one layer of sheet material and the sheet material of the next layer.

4. The combination of claim 3 and wherein the sheet material, culture medium, and barrier are rolled so as to form a body of substantially cylindrical configuration, said means being in the form of a casing which encapsulates the body of cylindrical configuration at all except the edge region of the sheet material which forms said one part of the wick.

5. The combination of claim 3 and wherein the layers are substantially parallel one with respect to the next, and said means encapsulating the substantially parallel layers for enclosing the same at all except the edge region of the sheet material which forms said one part of the wick.

6. The combination of claim 1 and wherein said wick is in the form of a sheet material and said culture medium having different portions of different properties respectively engaging different portions of the sheet material so that when the body fluid becomes situated at the different portions of sheet material the different portions of the culture medium will encourage the growth of different microorganisms, so that a test can be made simultaneously for a number of different microorganisms.

7. The combination of claim 6 and wherein said one part of said wick is formed by an edge region of the sheet material, said opposed part of the wick being formed by an edge region which is opposed to the edge region which forms said one part thereof, and the culture medium extending from said one part of the wick toward but terminating short of said opposed part of the wick with said portions of the culture medium respectively having in engagement with the wick separated narrow sections at said one part of the wick and separated sections respectively widening out from said narrow sections and situated at different distances between said parts of the wick.

8. The combination of claim 1 and wherein the wick includes an elongated portion adapted to be introduced into a body cavity and terminating in said one part of the wick while said wick has extending from said elongated portion an additional elongated portion adapted to be situated at the exterior of the body and terminating in said opposed part of the wick, said additional elongated portion being engaged by the culture medium, and said means enclosing said culture medium and said additional elongated portion of the wick.

9. The combination of claim 1 and wherein said wick, culture medium and means are incorporated into a tampon.

* * * * *